United States Patent [19]

Hyman

[11] Patent Number: 4,550,713
[45] Date of Patent: Nov. 5, 1985

[54] METHOD AND APPARATUS FOR OPPOSING DEFORMITY, DISPLACEMENT, AND EXPULSION OF THE OCULAR TISSUES DURING OPEN EYE SURGERY

[76] Inventor: Frederic E. Hyman, 40 E. 9th St., New York, N.Y. 10003

[21] Appl. No.: 474,812

[22] Filed: Mar. 10, 1983

[51] Int. Cl.$^4$ ............................................. A61B 17/00
[52] U.S. Cl. ................................ 128/1 R; 128/303 R
[58] Field of Search ............... 128/1 R, 645, 648–652, 128/745, 132 R, 134, 28, 30, 30.2, 303 R, 132 D, · 20

[56] References Cited

U.S. PATENT DOCUMENTS

| | | | |
|---|---|---|---|
| 3,186,300 | 6/1965 | Littmann | 350/515 |
| 3,492,987 | 2/1970 | Parker | 128/1 R |
| 3,612,468 | 10/1971 | Hoppl | 248/405 |
| 3,868,171 | 2/1975 | Hoppl | 350/85 |
| 4,014,342 | 3/1977 | Staub | 128/305.1 |
| 4,108,182 | 8/1978 | Hartman | 128/305 |
| 4,184,492 | 1/1980 | Meinke | 128/303.14 |
| 4,275,719 | 6/1981 | Mayer | 128/1 R |
| 4,275,733 | 6/1981 | Marinoff | 128/303 R |
| 4,326,306 | 4/1982 | Poler | 128/303 R |
| 4,376,437 | 3/1983 | Sundheim et al. | 128/132 R |
| 4,453,546 | 6/1984 | Katz et al. | 128/303 R |

OTHER PUBLICATIONS

Steve Charles, "Vitreous Microsurgery" (1981), pp. 33–35, FIGS. 3.24 and 3.25, and p. 53.
Richard C. Troutman, "Microsurgery of the Anterior Segment of the Eye" (1974), pp. 15, 19.
Weck, Optical Product Bulletin Nos. 004, 016.

Primary Examiner—Lee S. Cohen
Assistant Examiner—Steven Falk
Attorney, Agent, or Firm—Wells & Wells

[57] ABSTRACT

Deformity, displacement and expulsion of the ocular tissues during eye surgery of the type in which there is a cut through the ocular wall, is opposed by the method and apparatus of this invention. According to the invention, the external surface of the eye is divided into two areas by defining a line on the external eye wall that forms a closed loop surrounding the sites where incisions through the eye wall are to be made or where cuts through the eye wall have already been made by traumatic injury. Then, according to the invention, air pressure higher than atmospheric is generated, when needed, in a work space outside the eye adjacent to that part of the external eye wall that lies within the closed loop, without compressing the external surfaces of the eye that lie outside the closed loop. The eye is concurrently stabilized against the applied pressure by attachment to a fixation device, usually at points along the line between the pressurized and non-pressurized zones of the external eye wall. In the presence of a cut through the eye wall, pressure above atmospheric in the work space is transmitted to the interior of the eye via the cut.

54 Claims, 16 Drawing Figures

METHOD AND APPARATUS FOR OPPOSING DEFORMITY, DISPLACEMENT, AND EXPULSION OF THE OCULAR TISSUES DURING OPEN EYE SURGERY

BACKGROUND OF THE INVENTION

1. Field of the Invention

This invention relates to new and improved methods and apparatus for opposing deformity, displacement, and expulsion of the ocular tissues during eye surgery. The method and apparatus are for use during eye surgical procedures in which an incision is made into an internal compartment of an eye. Such eye surgical procedures include various types of corneal, cataract, vitreous, retinal, and glaucoma surgery. The method and apparatus are also for use during eye surgical procedures to repair an eye already cut open by traumatic injury. The method and apparatus also provide a means of regulating pressure within the eye during surgery. The method and apparatus also provide a means of filtering and humidifying the air in the vicinity of the open incision. The particular surgical case must be evaluated to determine whether or not the use of the method and apparatus is appropriate.

2. Description of the Prior Art

The state of the art of methods and apparatus for performing eye surgery may be ascertained in large measure by reference to U.S. Pat. Nos. 3,186,308; 3,612,468; 3,868,171; 4,014,342; 4,108,182; 4,184,491; 4,019,514; 4,157,718; 4,041,947; 4,168,707; 4,184,510; 4,184,492; 4,180,074; and 3,572,319; "Vitreous Microsurgery" by Steve Charles (Williams & Wilkins, Baltimore, 1981); "Surgery of the Eye" by E. D. Dorrell (Blackwell Scientific Publications, London, 1978); "Cataract Surgery and Its Complications" by Norman S. Jaffe (C. V. Mosby Company, St. Louis, 1981); "An Atlas of Ophthalmic Surgery" by John Harry King, Jr. and Joseph A. C. Wadsworth (J. B. Lippincott Company, Philadelphia, 1981); "Microsurgery of the Anterior Segment of the Eye" by Richard C. Troutman (C. V. Mosby Company, St. Louis, Volume I, 1974, Volume II, 1977); and Weck Optical Product Bulletins, "016 XY Translation Arm (1981)" and "004 XY Translation Table" (Edward Weck & Company, Inc., Box 12600, Research Triangle Park, N.C. 27709), the disclosures of which are incorporated herein.

Many surgical procedures are employed to restore, preserve, or improve vision. Some of these, including cataract surgery and penetrating keratoplasty (corneal transplantation), require that a surgical incision be made into the tissues and compartments of the eye. Before such an incision has been made, an eye with a normal intraocular pressure of about 15 mm Hg. above atmospheric maintains a steady resistance to deforming forces. Even an eye with an intraocular pressure measuring zero relative to atmospheric pressure can, before an incision is made into the intraocular compartments, offer considerable resistance to transiently applied forces by responding with a transient rise in intraocular pressure. However, an eye with a cut connecting its internal compartments with the operating room space at ambient atmospheric pressure has lost most of its ability to resist deformation because the ocular tissues can flow out through the opening, unimpeded, as a deforming force is applied. Various deforming forces bear upon the eye at various times during surgery. Thus, when a surgical incision is made, there is a tendency for the eyeball to assume a distorted shape and for fluid and tissue to be displaced towards the incision and to be expelled from the eyeball through the incision. The deformation results from the action of gravity on the tissues and fluids of the eye, from the contraction of the normally stretched elastic fibers of the ocular wall, from the pull of muscles fastened to the outside of the eye, and from the effect of compressed orbital structure. The deformation can also result from the pressure of surgical instruments laid on the eye or the orbit. Furthermore, when the surgical incision is made, the pressure within the eye, which, in a normal eye, is about 15 mm Hg. above atmospheric, falls towards atmospheric pressure, i.e., towards the ambient pressure in the operating room. This fall of the intraocular pressure favors seepage or "transudation" of fluid from the lumens of capillaries in the structures of the eye, through the capillary walls, and into the tissues and compartments of the eye. The fall in intraocular pressure also favors the occurrence of intraocular hemorrhage due to the failure of support for weak points in the walls of blood vessels of the eye which then rupture. Both transudation and hemorrhage contribute to internal deformation and loss of tissue or fluid through the incision. If a choroidal hemorrhage of sufficient magnitude occurs, the entire contents of the eye, including the retina, can be rapidly and unavoidably expelled, resulting in loss of the eye. In general, the greater the ocular deformity taking place during surgery, the greater the ocular damage, the greater the difficulties encountered by the surgeon, and the poorer the results of the surgery.

Various methods of dealing with the problems of intraocular hypotension, anterior (forward) displacement of the contents of the eye towards and through the incision, and ocular deformity during surgery have been described.

One such method attempts to maintain the intraocular pressure above atmospheric pressure by forcing fluid into the eye through a needle or cannula. As a result of the maintenance of this pressure differential between the inside of the eye and the air in the operating room while the eye is cut open, there is a tendency for fluid or tissue to be pushed out through surgical incisions, be they for the insertion of microsurgical instruments or for the infusion cannula itself. The size and position of the various incisions as well as the position of the infusion cannula influence to a considerable degree the tendency for fluid or tissue to be extruded. Since it might harm the eye if tissue prolapses, if excessive leakage prevents pressure maintenance, if excessive leakage requires excessively high infusion and intraocular flow rates, or if excessive leakage obscures the surgeon's view, the incisions must be kept small, plugged, or blocked. Even with small incisions, the possibility that tissue will prolapse exists, especially during insertion and removal of an instrument.

In situations where a large incision is necessary, it is sometimes possible to reduce the blood pressure of the patient so as to reduce the risk of expulsive hemorrhage or significant transudation. However, manipulation of the blood pressure may compromise circulation of blood to the brain, the heart, the kidneys, as well as to the eye itself.

External mechanical support can be provided for the sclera, i.e., the ocular coat, at a finite number of points by attachment of a Flieringa ring, a scleral expander, or the like, around an anterior part of the eye. However, there is little support for the rearward portions of the eye because such external supports are sewed only to the exposed parts at the front of the eye. The effect of hemorrhage or transudate can still be to separate the choroid and the retina from the sclera because of failure of the external support to provide appositional force between these structures. Finally, such external skeletal supports may create undesirable stresses by supporting the sclera at the same time that the elastic choroid tends to collapse and fall away from it.

Other methods are also employed to reduce anterior displacement by producing a "soft eye", i.e., an eye which has an intraocular pressure lower than normal, before the incision is made. Such methods include compressive ocular massage, intravenous infusion of osmotic agents to draw water out of the body tissues, and the use of a needle to aspirate liquid vitreous. These measures reduce the ocular volume thus relieving compressive forces so that there will be less resulting anterior displacement of the ocular contents towards the incision when the incision is finally made. Paralyzing the ocular muscles with drugs such as intravenous curare is also employed. (Osmotic agents, liquid vitreous aspiration, and drugs such as curare are sometimes used after the incision is made.) These softening techniques have side effects and risks which are well known.

It is an object of this invention to provide the surgeon with a method and apparatus for maintaining desired anatomical relationships during the performance of surgery through an open incision of a size appropriate to the surgical task to be performed.

DEFINITION

By "designated surgical field" is meant a portion of the eyeball surface, designated by the surgeon in a particular case, through which all incisions through the eyeball wall are to be made, through which all traumatic injury cuts through the eyeball wall are present, and through which all internal manipulations inside the eye are to be performed.

It should be understood that during the attachment of the invention apparatus to the eye, access to a slightly larger area than the area designated as the "designated surgical field" will be required.

It should also be understood that in dividing the eyeball surface into an area constituting the "designated surgical field" and an area outside the "designated surgical field", for practical purposes, between the two areas there will be a boundary line, border, or periphery of finite width to which structures may be attached without significantly encroaching on either of the two principle areas. For clarity, in the description of the invention and in the claims, each of the three zones is specifically referred to when necessary.

SUMMARY OF THE INVENTION

The method and apparatus of this invention oppose deformity, displacement, and expulsion of the ocular tissues during eye surgery of the types in which a cut is present through the ocular wall by (a) generating an air pressure higher than atmospheric pressure in a space outside the eye that bears upon the designated surgical field;

(b) concurrent with step (a), maintaining those surfaces of the eye that lie outside the border of the designated surgical field at ambient atmospheric pressure;

(c) concurrent with steps (a) and (b), stabilizing the eye against the applied pressure; and (d) concurrent with steps (a), (b), and (c), providing access of the surgeon to the designated surgical field.

In a preferred embodiment of the invention, an enclosed air space is provided with an aperture the edges of which are attached to the eye along a line that encompasses the site of the surgical incision to be made. By pressurizing the enclosed space, pressure is maintained in the vicinity of the proposed incision site, and in the eye after the surgical incision has been made, but not on the external surfaces of the eye outside the enclosed space which continue to be at ambient atmospheric pressure. To this end, with the patient lying face up on an operating room table, with his head stabilized to an underlying base plate, a pressurizable chamber is assembled and supported over the patient's face with its rigid parts deriving support from the base plate. The walls of the chamber consist in part of flexible material which is draped over the patient's face. The edges of an aperture in the drape are attached to the eye along the border of the designated surgical field. In this embodiment, the attachment of the drape aperture to the eye is by means of a rigid ring sewn to the eye, the drape aperture edges being sewn to the ring. The position of the ring is adjusted and immobilized by a suitable support apparatus. The ring and its support apparatus serve the function of immobilizing the junction of the eye and the flexible drape. When the chamber is pressurized, the air pressure within it exerts force against the surface of the eye within the circle of the sutured ring, i.e., against the designated surgical field. Normally, pressure against an anteriorly directed surface of the eye would result in posterior movement of the eye into the orbital fat cushion behind the eye. The immobilized ring sutured to the eye serves to prevent such movement. The ring is also equipped with lateral projections passing between the drape and those surfaces of the eye that lie outside the circle of the sutured ring. When the chamber is pressurized, the air within it exerts force against the surfaces of the drape peripheral to the aperture. However, the ring projections passing beneath the drape insure that the drape is not forced down against those parts of the eye that lie outside the circle of the sutured ring. Portals in the chamber walls permit access of the hands of the surgeons to the designated surgical field. Hermetic seals from the portal edges to the surgeons' forearms prevent excessive leakage of air out of the chamber. Airlocks permit instruments or surgical materials to be passed into and out of the chamber without substantial loss of pressure. Air inlet and outlet openings are provided and used for pressure regulation. Parts of the chamber walls are transparent to permit visual access to the surgical field, and optical devices can be built into the walls of the chamber for observation purposes.

The method and apparatus of the invention thus provide for maintenance of intraocular pressure above atmospheric even when a large incision is used. The pressure is transmitted across the incision to the interior of the eye without applying additional pressure to the external surfaces of the eye outside the border of the designated surgical field. This tends to maintain the normal shape and volume of the eye against deforming forces in a manner that mimics the natural state of the eye. There is an appositional force between the vitreous, the retina, the choroid, and the sclera. The pressure maintained within the eye opposes transudation and hemorrhage. All of the above tends to keep the ocular tissues in their normal anatomic positions and to prevent displacement of the ocular contents towards and through the incision.

The invention contrasts with those methods discussed previously which "soften" the eye before surgery, all of which fail to oppose transudation and hemorrhage, and most of which deform the eye. As stated previously, the side effects and risks of the known procedures are well known and, in many patients, contraindicate their use.

The invention contrasts with those methods discussed previously which attempt to maintain ocular shape and volume by sewing a relatively rigid system of interconnecting rings or wires to the outside of the eye at a finite number of points on the exposed anterior surfaces of the eye. Though often of considerable benefit, such "exoskeletons" do not support the eye posteriorly, do not provide appositional forces between retina, choroid, and sclera, and do not oppose transudation and hemorrhage.

The invention contrasts with pharmacologic lowering of blood pressure as a means of reducing hemorrhage and transudation because the invention produces its effect by correcting the causative abnormality, namely, intraocular hypotension, rather than by introducing a possibly dangerous compensatory abnormality.

The invention contrasts with the hypothetical use of a hyperbaric chamber that might encompass the entire head of the patient. While such a chamber would increase pressure on the ocular tissues and might oppose transudation and hemorrhage, it would fail to support the natural shape and volume of the eye because it would not retain the pressure differential between the inside of the eye and the external surfaces of the eye. The invention achieves such a differential pressure between the inside of the eye and all those external ocular surfaces lying outside the border of the designated surgical field. Thus, unlike the hypothetical hyperbaric chamber just mentioned, the invention tends to support the natural shape and volume of the eye.

The invention also contrasts with methods previously employed to maintain intraocular pressure above atmospheric. As stated previously, with these other methods, the pressure elevation is effected by a cannula introduced into the eye, leaving the pressure outside the eye in the vicinity of the incision at atmospheric. This results in a requirement that the incision be kept small, reduced in size, plugged, or otherwise blocked, and also results in a tendency for tissue to prolapse, in spite of the small incision size, especially during insertion and removal of instruments. Unlike these other methods, this invention does not generate a difference in pressure across the incision which is higher inside the eye than outside because the primary elevation in pressure is generated in a work space outside the eye in the vicinity of the incision, and is transmitted secondarily to the inside of the eye via the incision. Since the invention does not generate a pressure differential across the incision higher inside the eye than outside, it does not create a tendency for tissue to prolapse and does not require a small incision. The invention enables the surgeon to maintain intraocular pressure during those procedures in which a large incision is either necessary or desirable as well as in those in which small incisions are used. In addition, the invention can be used to great advantage in repairing traumatic wounds of the eye, large or small, by aiding in restoring and maintaining normal anatomic relationships during the repair. The need to properly place and monitor the position of pressure cannulas lest they damage the eye during the surgery, and the need to provide accurate and sensitive feedback mechanisms for precisely controlling the amount of fluid injected into or aspirated from the eye, are obviated by the invention.

In summary, the method and apparatus of the invention provide the eye surgeon with a means while performing surgery to maintain a desired pressure in a defined space into which the incision opens externally, and to transmit this pressure via the incision to the internal compartments of the eye without exerting undue pressure on external surfaces of the eye that lie outside the field of the incision. Liquid and tissue egress, displacement of the ocular contents towards the incision, ocular deformation, and transudation and hemorrhage are all thereby opposed and desirable anatomic relationships are maintained, facilitating the performance of surgery through an open incision of a size appropriate to the surgical task to be performed.

The method and apparatus of the invention may also be used to reduce exposure of the eye to dust, to air pollutants, and to microbial contamination during surgery, thus reducing exposure to potential complications that may lead to blindness.

DETAILED DESCRIPTION OF THE INVENTION

The following is a description of a preferred embodiment of the invention describing the application of the invention to a patient. Some variations are included.

Figure 1:
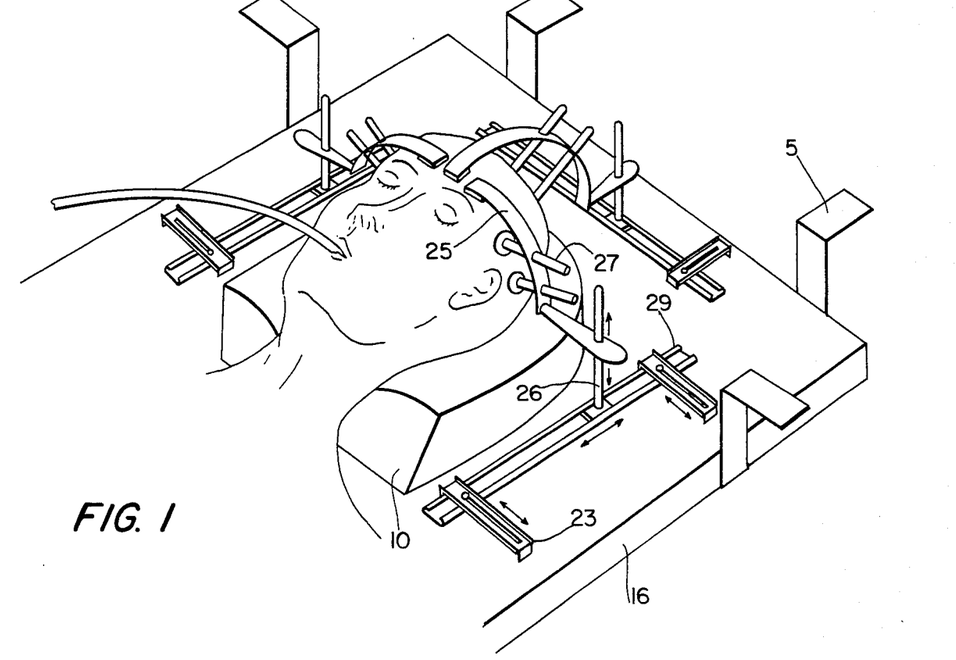
FIG. 1 shows stabilization of a patient's head on a base plate prior to assembly of the apparatus.

The pictorial view of FIG. 1 shows the head of a patient who is lying on an operating room table. The patient's head is resting on a firm head rest 10 that has been fixed to a rigid base plate 16 that rests on the operating room table. The patient has been anesthetized, and an anesthesia airway tube is shown entering the patient's mouth. The head is shown to be stabilized by head braces 25 applied after the induction of general anesthesia. The padded tips of the head braces press down against the patient's forehead. The braces are supported on posts 26 attached to the base plate. The vertical height of each brace is adjustable. The position of the supporting post is adjustable along track 29. The position of the track itself is adjustable on the base plate under guide bars 23. Threaded rods 27 engaged in threaded holes passing through the braces compress pads against the head to add further stability. Thus, in FIG. 1, head stability is achieved by a combination of general anesthesia and mechanical support. Though head stability is important in any surgical procedure, and though the precise manner in which head stability is achieved is not important, head stability is an integral part of this embodiment because the position of the head must be stabilized in relation to the position of other parts of the apparatus, particularly those parts that are attached to the eye. For the sake of clarity, all of the head stabilizing parts shown in FIG. 1 are not shown in the other figures, but it should be borne in mind that the head is stabilized to the base plate.

Part of an eye surgical procedure usually includes cleansing the area of the eye with antiseptic solutions, and covering the face and body of the patient with sterile cloths except for a small cleansed area around the eye. These details are not shown in the drawings. However, it should be clear from FIG. 1 that there is adequate access to the patient for the performance of these tasks.

Figure 2A:
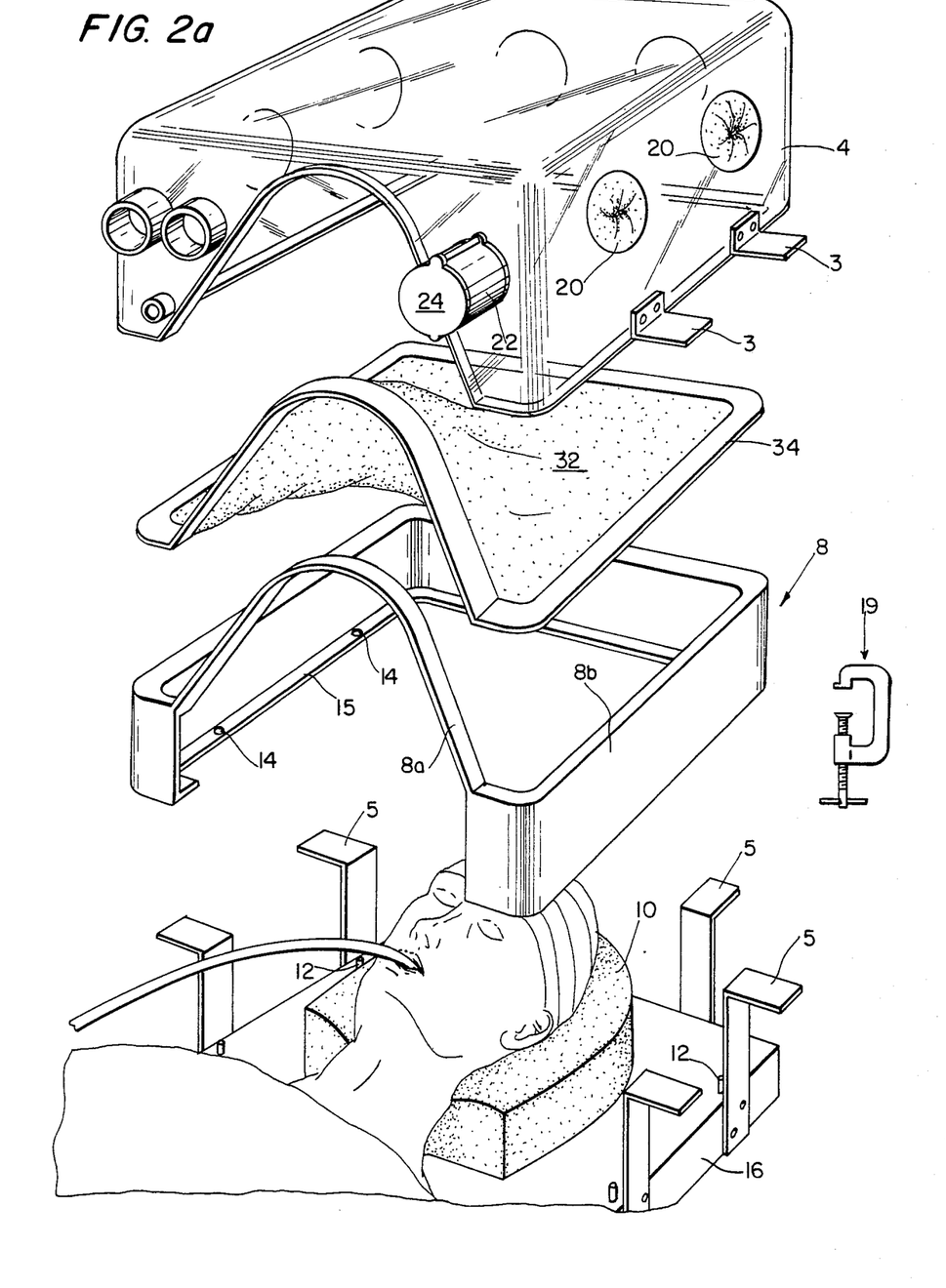
FIG. 2a is an exploded view of the apparatus of a preferred embodiment.

FIG. 2a shows an exploded view of a pressure chamber that can be assembled over the patient's eye in stepwise fashion.

Base frame 8 consists of archlike part 8a and U-shaped part 8b. Base frame 8 is lowered onto base plate 16 so that U-shaped part 8b surrounds the head of the patient on three sides with the opening in the U allowing for passage of the patient's neck. Archlike part 8a connects the ends of the U, and bridges over the opening in the U. Base frame 8 is anchored against lateral motion by pins 12 that pass upwards from base plate 16 into mating holes 14 in footing 15 of base frame 8.

As shown in FIG. 2a, flexible drape 32, which may be of plastic material such as medical grade vinyl, is attached to frame 34. Frame 34 has a downwardly facing surface mated to the upwardly facing surface of base frame 8. Frame 34 also has an upwardly facing surface that is parallel to its downwardly facing surface. Frame 34 is emplaced on base frame 8. Then, upper enclosure 4, which has a downwardly facing rubber gasketed surface matched to the upwardly facing surface on frame 34, is emplaced on frame 34. Upper enclosure 4, drape 32 with attached frame 34, base frame 8, and base plate 16 are then clamped together. This is achieved by clamping angle irons 3, attached to upper enclosure 4, to angle irons 5, attached to the base plate, using small C clamps 19.

Figure 2B:
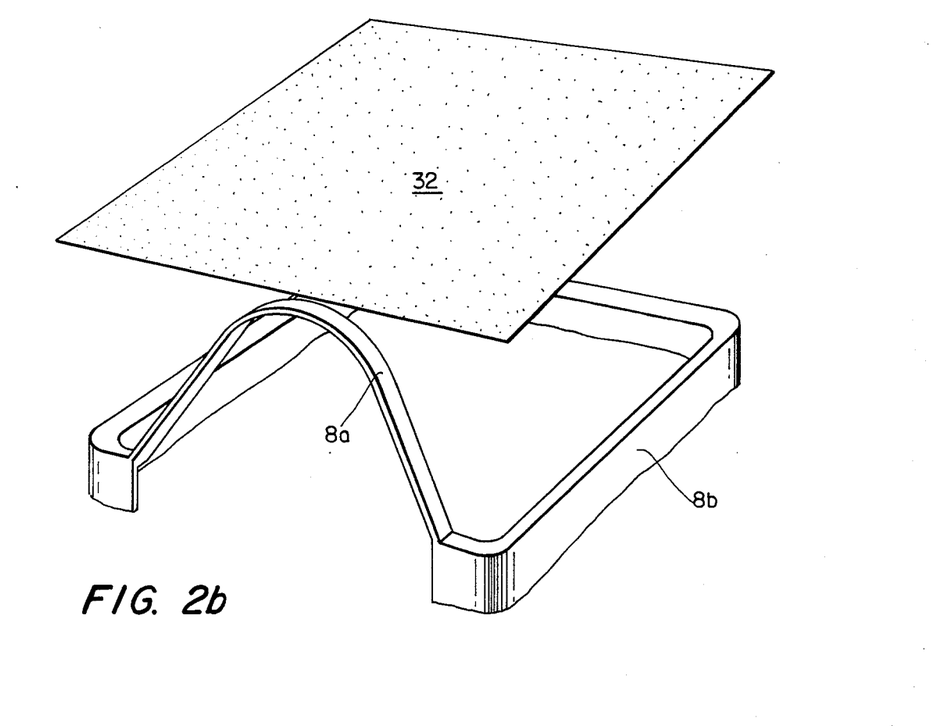
FIG. 2b is another embodiment of FIG. 2a showing the drape without a reinforced edge.

FIG. 2b shows an alternative mode of construction, differing only in that a drape without an attached frame 34 is used. In this case, after base frame 8 is emplaced, the drape is laid over the base frame. The upper enclosure is then emplaced, and the elements clamped together. The upper surface of base frame 8 forces the peripheral parts of the drape against the matching downwardly directed surfaces of the upper enclosure, sealing the drape to the upper enclosure.

Figure 3:
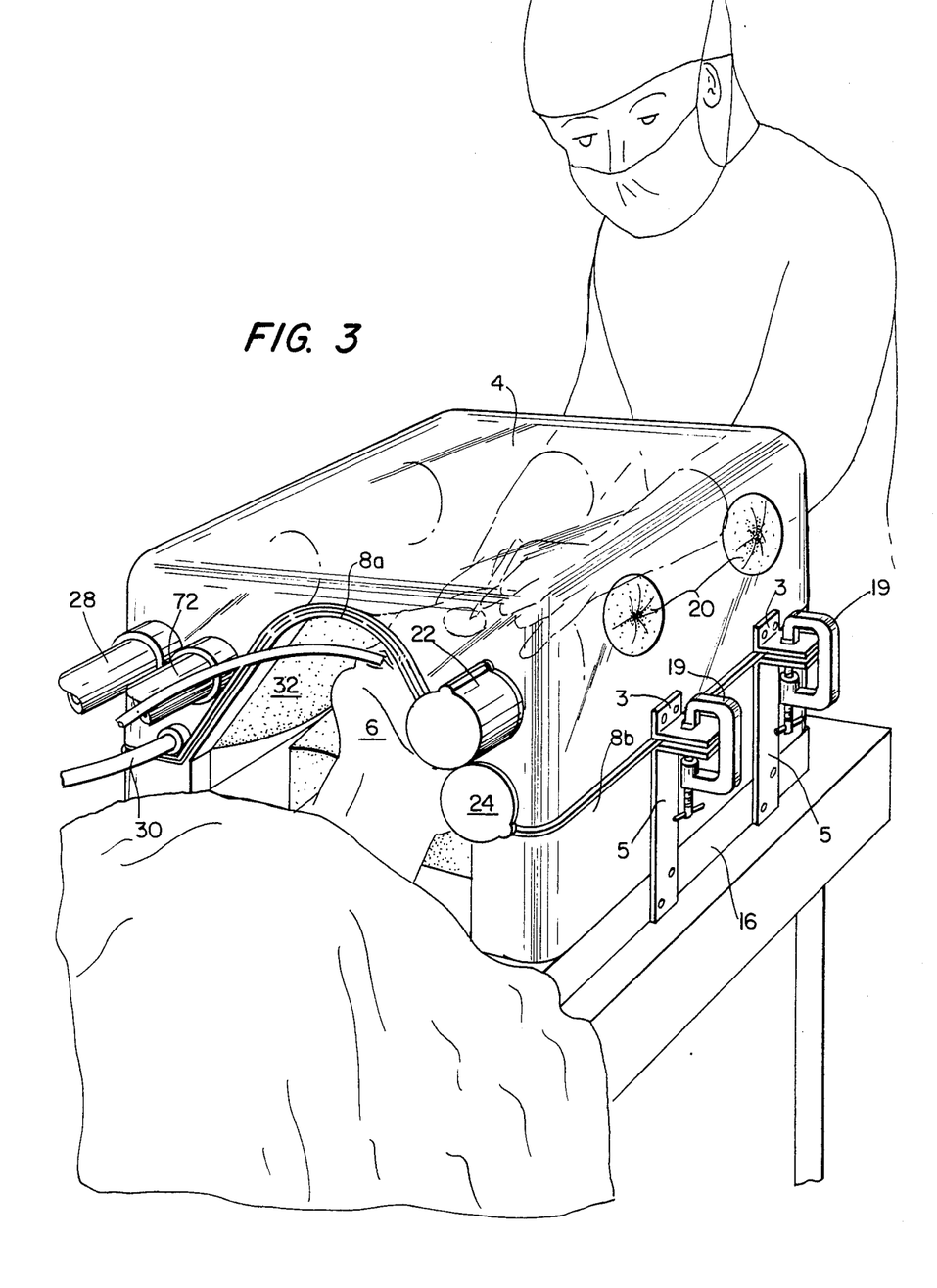
FIG. 3 shows the apparatus of FIG. 2a in use during surgery after assembly and clamping together of its parts.

FIG. 3 shows the appearance of the assembled pressurizable chamber composed of the parts shown in FIG. 2a. Although at first glance it might appear that the head of the patient lies within the chamber, it should be remembered that the head of the patient lies outside the chamber below the flexible drape. Note in FIG. 3 that the archlike part of base frame 8 (part 8a) supports the drape in such a manner that there is clearance over the patient's mouth for the anesthesia airway tube which can be checked when necessary by the anesthesiologist during the procedure. Note also that the slope of the archlike structures is nowhere vertical, because, when the clamps are applied, the forces compressing the chamber elements together are vertically oriented. Thus, there will be compression between all points in contact along the mated surfaces. Note also that the hands of the surgeons gain access to the pressurizable chamber through hermetic port seals 20 in the side walls of upper enclosure 4. Upper enclosure 4 may be of transparent plastic permitting the surgeons visual access to the inside of the chamber. The microscope objective may remain outside the chamber or be sealed into it. Note also in FIG. 3 the presence of air inlet hose 28 penetrating the wall of the chamber, providing a passageway for air for maintaining pressure above atmospheric in the chamber. Air outlet hose 72 also penetrates the wall of the chamber providing a passageway for air to leave the chamber. Another tube 30 is shown penetrating the wall of the chamber, and represents tubing connecting an instrument to be used inside the chamber, such as a cryoprobe hand piece, with apparatus or power supply that is to remain outside the chamber. Hermetic seals permit passage of tubes or cables into the chamber. Additional hermetic seals can be added for other special instruments. Small instruments and surgical material are passed into and out of the chamber through an airlock 22 mounted in a wall of upper enclosure 4. The airlock is provided with doors 24 at each end which can be operated in sequence to permit passage of instruments or surgical material without substantial change of pressure within the chamber. An instrument rack 36 (FIG. 4a) mounted on the inside wall of upper enclosure 4 reduces the need to use the airlock.

Figure 4A:
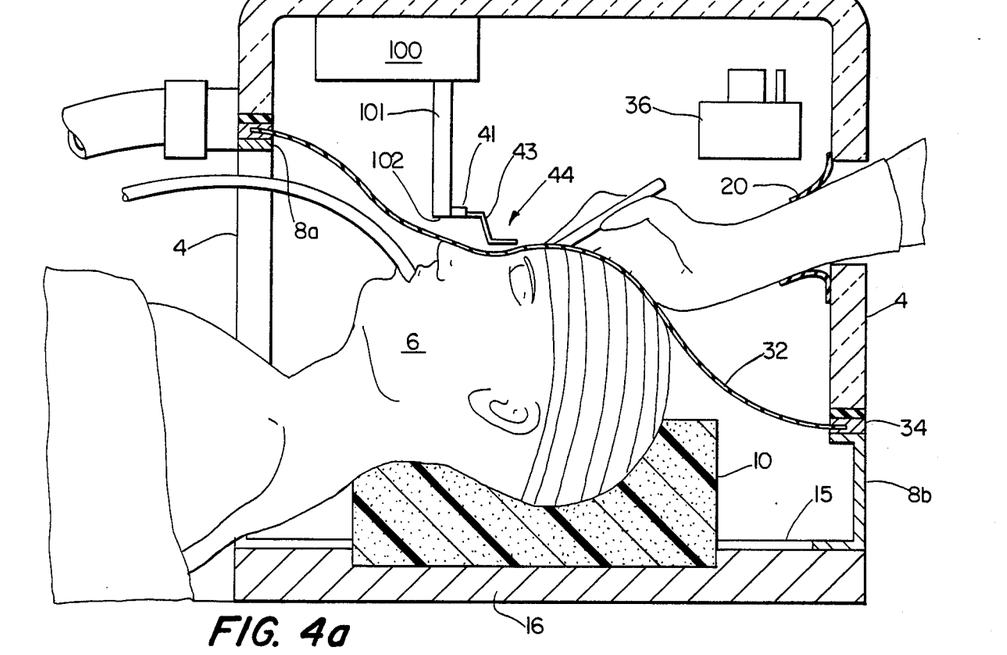
FIGS. 4a and 4b are, respectively, longitudinal and transverse sections of the assembled apparatus of FIG. 3 showing further details.
Figure 4B:
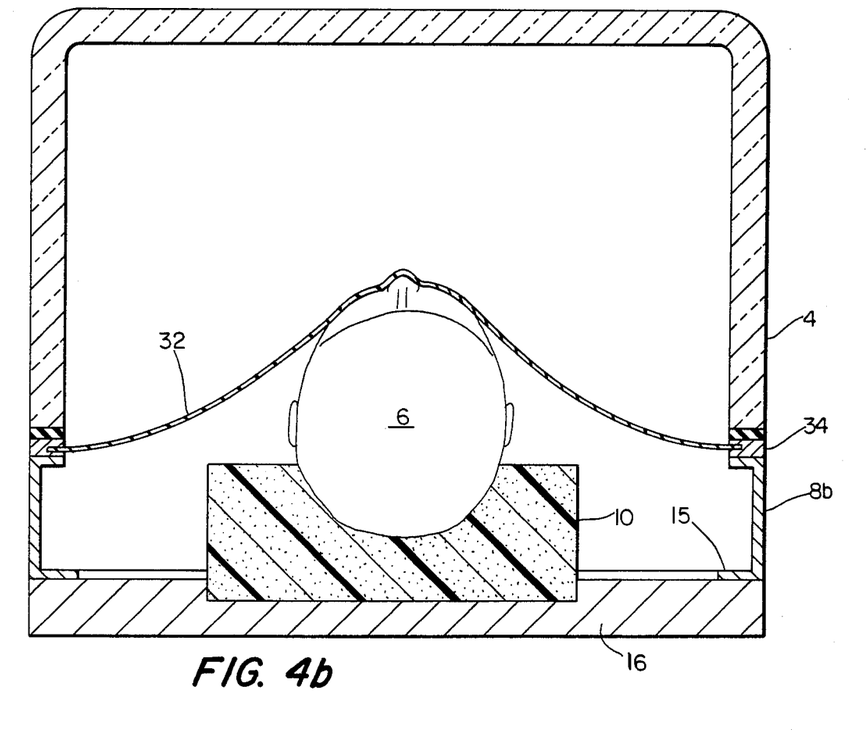
Figure 5:
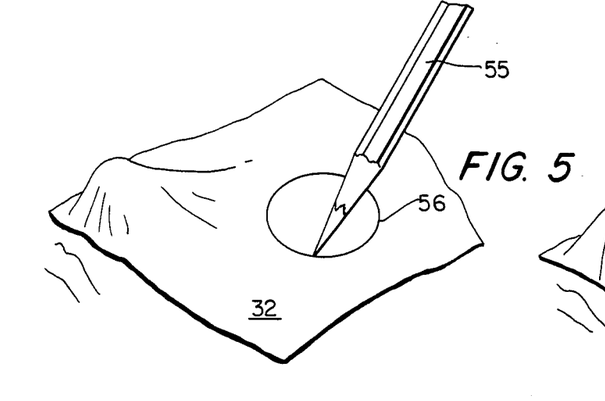
FIGS. 5 through 8 are partial views showing successive steps in the formation of an aperture in a flexible drape and coupling of the aperture edges to the eye.
Figure 6:
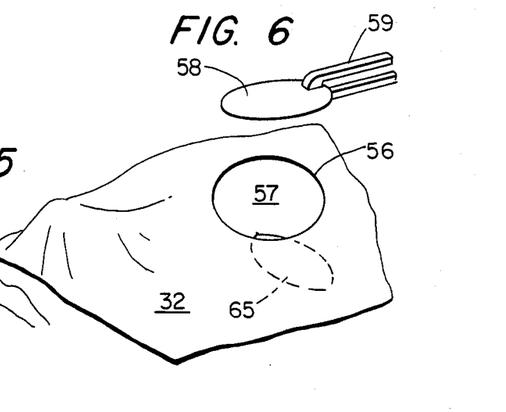

FIGS. 4a and 4b further depict the relationship of the apparatus, of the embodiment being described, to a patient. Note that the surgeons' hands lie inside the pressurizable chamber above the flexible drape, while the patient and his eye lie outside the chamber below the drape. In this embodiment, the pressure in the chamber is then elevated above atmospheric causing the flexible drape to lie against the patient's face, and to assume to some degree the contours of the patient's face. The surgeon then marks the portion of the drape lying over the patient's eye. FIG. 5 shows a marking pen 55 making a circular mark 56 on drape 32 over the patient's eye. Then the chamber pressure is reduced to atmospheric. The surgeon then lifts the drape away from the eye 65, and cuts a hole in the drape where it had been marked, giving him direct access to the eye. FIG. 6 shows portion 58 of drape 32 being removed with forceps 59 leaving hole 57 in drape 32.

Figure 7:
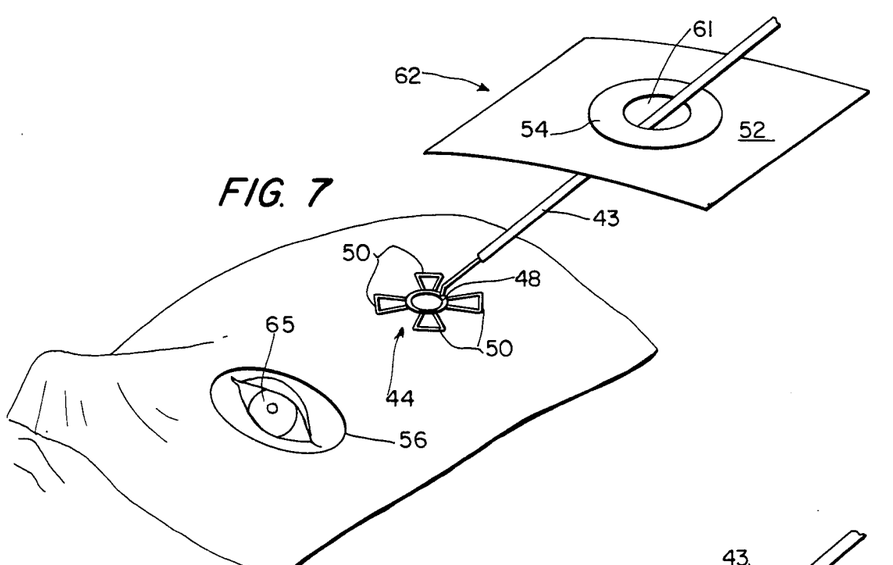

In this embodiment, as shown in FIG. 7, a specialized support ring 44 with its attached stem 43 is positioned over the eye 65 prior to lowering this ring through hole 57 onto the eye. Also shown in FIG. 7 is flexible adhesive patch 62 positioned so that the stem 43 of ring 44 passes through aperture 61 of patch 62.

Stem 43 is received and clamped by chuck 41 shown in FIG. 4a. Chuck 41 is carried by chuck carrier bar 101 which is connected to adjustable, but otherwise rigid X, Y, and Z support mechanism 100 manipulated by the surgeons to position ring 44, laterally, longitudinally, and vertically relative to the patient's eye. This X, Y, and Z support mechanism 100 of this embodiment incorporates the mechanisms disclosed in one or more of U.S. Pat. Nos. 3,186,300, 3,612,468, and 3,868,171, and WECK Optical Product Bulletins, "016 XY Translation Arm (1981)" and "004 XY Translation Table". X, Y, and Z support mechanism 100 is attached to the inside wall of upper enclosure 4. It should be noted that although FIG. 4a depicts the body of ring 44 in the horizontal plane, rings with stems attached at different angles can be provided to fulfill the requirements of different surgical procedures. Also, angulation can be provided by substituting a lockable joint for rigid elbow 102.

Figure 8:
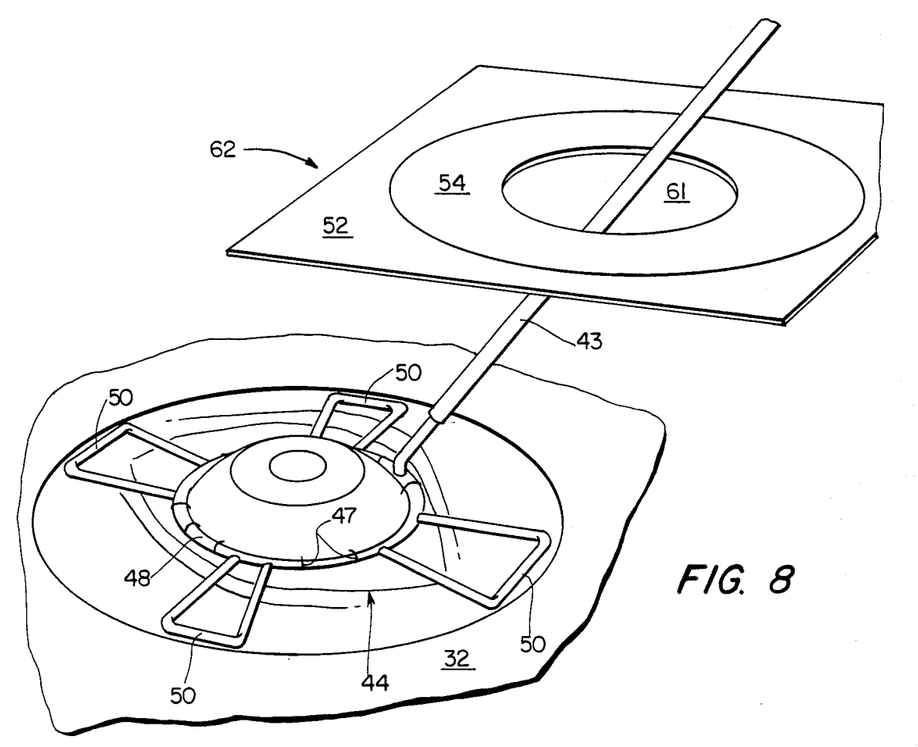
Figure 9:
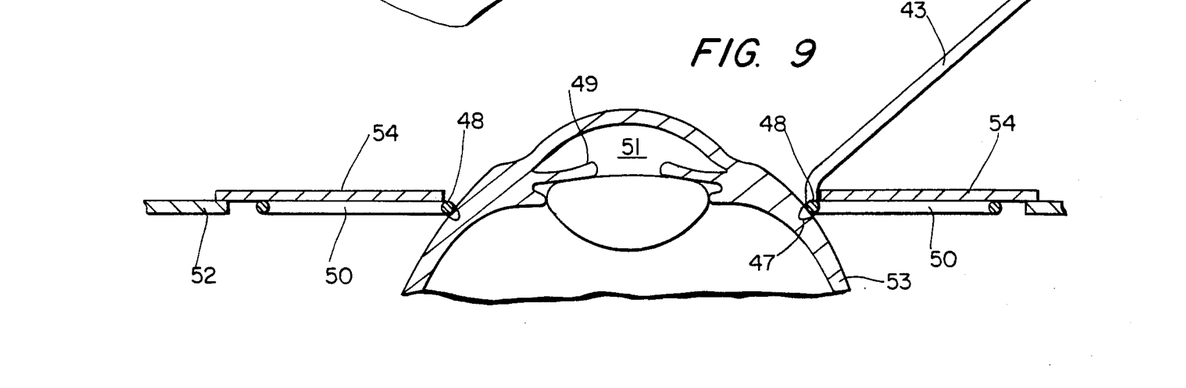
FIG. 9 is a view in cross-section of an eye with a supporting ring and the drape in place.

The surgeon positions support ring 44 onto the eye, and fastens it to the eye with sutures. See FIGS. 8 and 9. In the embodiment shown, ring 44 has body 48 whose cross section is circular as shown in FIG. 9. The sutures 47 engage the ocular wall 53, and are looped and tied around the body 48 of ring 44 securing the ring to the eye as shown in FIGS. 8 and 9. In this embodiment, the ring body forms a closed loop which is circular, which lies in the horizontal plane, which has a diameter larger than that of the anterior chamber 51 (FIG. 9) of the eye, and which is attached symmetrically to the eye wall near the junction of the cornea and the sclera.

Flexible patch 62 includes square 52 of flexible plastic material which has, for example, a pressure sensitive adhesive coating (not shown) on its lower surface. The patch can be caused to adhere to the upper surface of drape 32 when brought into contact with it. The center of square 52 has been cut away to receive flexible elastic disk 54 which is assembled to it prior to use of the patch. Disk 54, which may be of rubber, is fastened to plastic square 52 by means of, for example, a pressure sensitive adhesive. Central aperture 61 in elastic disk 54 is matched to the circumference of body 48 of support ring 44 so that when attached thereto, e.g., by sutures, a substantially hermetic seal is afforded.

The surgeon slides flexible patch 62 down stem 43 bringing the edges of aperture 61 into apposition with the body 48 of support ring 44. He apposes the adhesive undersurface of the patch to drape 32 closing hole 57. He sutures the edges of aperture 61 to the body 48 of ring 44. Note that the patch rests on the horizontal projections 50 attached to the body 48 of ring 44 as shown in FIG. 9. The surgeon is now ready to proceed with surgery. By controlling the air pressure in the enclosed space, it is now possible to apply controlled air pressure to the designated surgical field inside the circle of the sutured ring whenever and to whatever degree this will serve his immediate surgical objectives.

The above-outlined procedure achieves the following purposes:

The use of relatively thin flexible drapery for the bottom of the pressurized chamber allows the bottom of the chamber to conform to facial contours, permitting maximum accessibility of the surgeon's hands to the eye of the patient, and allowing for the variation in facial contour from one patient to another.

The use of immobilized ring 44 with attached lateral projections 50 makes possible the safe and effective use of the flexible drape as the bottom of the pressure chamber. The attachment of the eye to an immobilized ring, rather than directly to the drapery without immobilization, prevents the eye under pressure from moving posteriorly against structures behind it. The lateral projections of the ring support the drapery, preventing it from compressing the eye. The attachment of the drapery hole edges to an immobilized ring rather than directly to the eye assures that pull on the drapery, e.g., lateral or upward, will not distort the eye. In particular instances, the laterally projecting arms may not be required. In such cases, support for the drape could be derived from the bony structures of the patient's face and from the connecting of the drape to the rest of the enclosure. Indeed, in particular instances, the immobilized ring itself, may not be required, the drape aperture edges being sewn directly to the eye, with support for the drape, its aperture edges and the eye being derived from the bony structure of the patient's face and from the connecting of the drape to the rest of the enclosure. Furthermore, appliances such as rubber pads may be placed on the patient's face to alter its contour in a way that favors support for the drape and its aperture. An adhesive undersurface on such appliances and under the drape itself will aid in positioning these structures.

The use of patch 62 as described enables the surgeon to position the drapery hole after the lie of the drape, i.e., the position of the drape under pressure, has been determined. This reduces any tendency for pressure applied to the drape to displace the hole from its proper position in relation to the eye. The use of patch 62, as described, conveniently enables the surgeon, while his hands are in the chamber over the drape, to manipulate the eye through a larger hole of adequate size during attachment of the junctional ring to the eye and adjustment of the support arm. Then the size of the hole is conveniently reduced to match the ring via the application of patch 62, sealing the chamber to the smaller circumference of the junctional ring. Prepositioning the patch on the stem of the ring, as shown, allows the support apparatus to be attached to the ring during attachment of the ring to the eye and afterwards.

Air pressure can now be applied to the designated surgical field, including the proposed incision site, without compressing the external surfaces of the eye that lie outside the border of the designated surgical field. As a consequence of this arrangement, when the incision is made, the pressure in the chamber is transmitted via the incision to the internal compartments of the eye, inflating the eye, so to speak, and providing forces like the normal internal appositional forces which act between the vitreous, the retina, the choroid, and the sclera, and opposing the forces which tend to deform the eye and to expel its contents.

Some other advantages of the invention are as follows:

Since the procedure described does not raise the pressure in the eye above the ambient pressure immediately outside the incision, the procedure does not generate a tendency for tissue of the eye to prolapse, as does pressurization via cannula where the pressure immediately outside the incision remains at atmospheric pressure.

The protection afforded is in place before any incisions have been made.

Since protection is afforded before the incision is made, there need be no drop in the intraocular pressure to atmospheric at any time while the eye is open for surgery, and consequently, those occurrences of expulsive hemorrhage and resultant total blindness that are triggered by a fall in intraocular pressure to atmospheric can be prevented. Many other significant hemorrhages can also be prevented.

Maintaining higher than atmospheric pressure in the eye opposes transudation of fluid from the circulatory system that deforms the ocular tissues and contributes to tissue displacement towards and through the incision.

By controlled application of pressure applied at the outset, the invention provides a means of gradually reducing the pressure in a glaucomatous eye (eye with abnormally high pressure) towards a desirable pressure that can be maintained during the surgical procedure.

The use of a continuous fluid flow within the eye itself or the insertion of a cannula tip within the eye itself, both of which may damage the delicate internal structures of the eye, are avoided.

Deformity, displacement, and expulsion of the ocular tissues during the performance of surgery in which a large incision is necessary or desirable, are opposed.

FIGS. 10 to 13 illustrate alternative embodiments of support ring 44, each embodiment being provided with a support stem 43 for immobilizing the ring.

Figures 10, 11, 12:
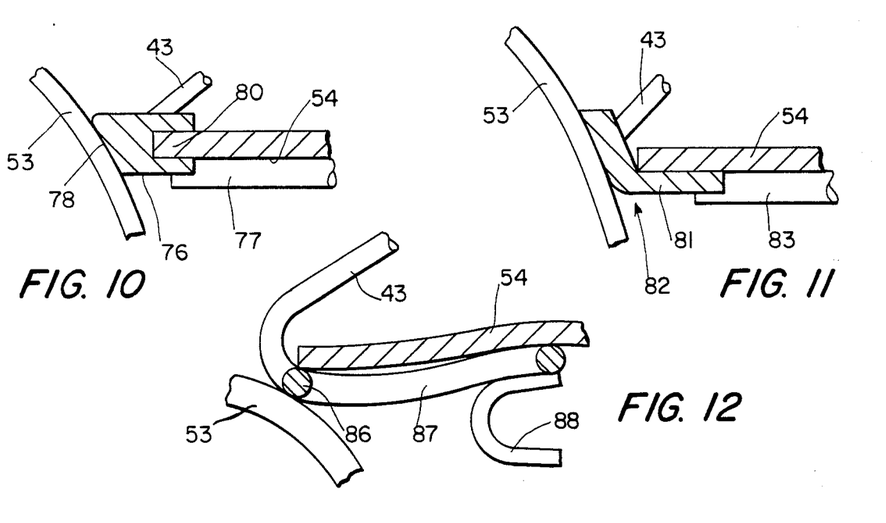
FIGS. 10 to 13 are views in cross-section of a number of embodiments of the supporting ring in place on a portion of an eye.

In the structure of FIG. 10, body 76 of the support ring is of trapezoidal cross-section and has an inner surface 78 adapted to conform to the profile of the sclera. The outermost face of body 76 is provided with slot 80 into which the central edge of rubber disc 54 can fit. The elasticity of disc 54 insures that it can easily be expanded to fit over the rim of body 76 and into slot 80, avoiding the need for sutures to connect the disc to the ring. Since the sutures used to connect the ring to the eye pass around the body of the ring crossing the slot, which would interfere with the rubber disc seating in the slot, the rubber of the disc can be prenotched or notched by the surgeon at the points where sutures holding the ring to the eye cross the slot. In the alternative, the ring can have vertical slots for the sutures.

Body 82 of the support ring shown in FIG. 11 has a generally L-shaped configuration, with the vertical part of the L leaning inwards over the anterior portion of the eye and generally conforming to the angle of the sclera. The horizontal leg of the L forms shelf 81 on which the inner edge of flexible rubber disc 54 can seat "with pressure" when the chamber is pressurized. Shelf 81 can be holed or slotted to accomodate sutures to prevent "bowstringing" across the open angle of the L.

The ring structures of FIGS. 10 and 11 are provided with laterally projecting arms 77 and 83, respectively, which, like arms 50 in FIG. 7, are for the purpose of keeping flexible drapery 32 and flexible patch 62 from pressing on the eye of the patient. The structures of FIGS. 10 and 11 are both designed to make a hermetic seal without the need for sutures between the ring and the drape. The angulation of the "petals" formed by projecting arms 77 and 83 can, of course, be adapted to particular situations.

The support ring shown in FIG. 12 has a body 86 like that of ring 44 in FIGS. 7 to 9, but is provided with outwardly extending support arms 87 which extend horizontally, as they leave body 86, and are then directed upwards, away from the orbit. Finally, they are directed back to the horizontal. This "S" configuration is useful for situations where the patient's eyes are deeply recessed in the face. As in the other rings, these lateral arms 87 function to insure that the drape does not transmit pressure to the eye at points outside the border of the designated surgical field. FIG. 12 also illustrates the use of hook-like wires 88 which are attached at the outer ends of lateral arms 87 to serve as retractors for holding the eyelids.

Figure 13:
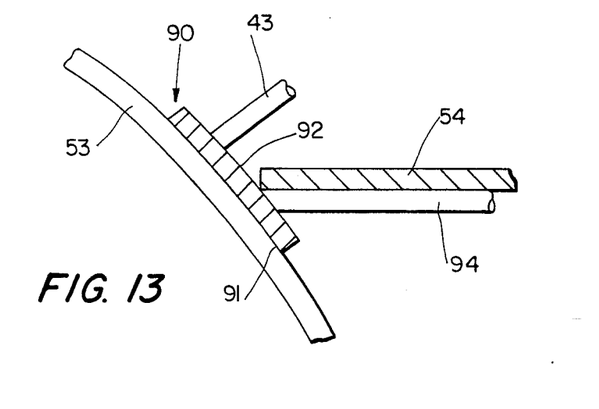

FIG. 13 shows a ring 90 of the Pierse type which has parallel sloping inner and outer walls 91 and 92, respectively, and which generally conforms to the slope of the sclera at the point of intended attachment. Stem 43 is fastened to the upper part of outer surface 92 and the inner edge of drapery disc 54 contacts the same surface below the stem, being supported on arms 94 which project laterally from a lower part of outer surface 92.

While the bodies of the rings depicted in the drawings are shown to be attached to the eye symmetrically about the anterior part of the eye close to the junction of the cornea and sclera, it will be understood that attachments to the eye in other locations may be required. For example, if a choroidal tumor at the equator of the eye is to be resected, the eye will be positioned to expose this area, and the ring will be applied to the eye around the area of the tumor location. It will be understood that rings of different diameters will be called for by particular situations. For example, if a keratoprosthesis is to be positioned in a central hole made in a severely scarred and vascularized cornea, a ring with a diameter smaller than the cornea may be sewn to the cornea. Furthermore, it will be understood that shapes other than circular may be required by particular surgical situations. The essential feature of the ring is that when resting on the eye, it forms a continuous linear zone of contact with the eye, this linear zone of contact forming a closed loop along the border of the designated surgical field. Note that the linear zone of contact with the eye of rings conforming to this definition need not be in a plane. When an irregularly shaped "ring" is used, the aperture in the drape will, of course, be shaped appropriately to give the needed hermetic closure at the junction. Also, it will be understood that, when using a ring of any configuration, the drape or any of its components may be specially pre-shaped to conform to the ring or to the patient's face.

Figure 14:
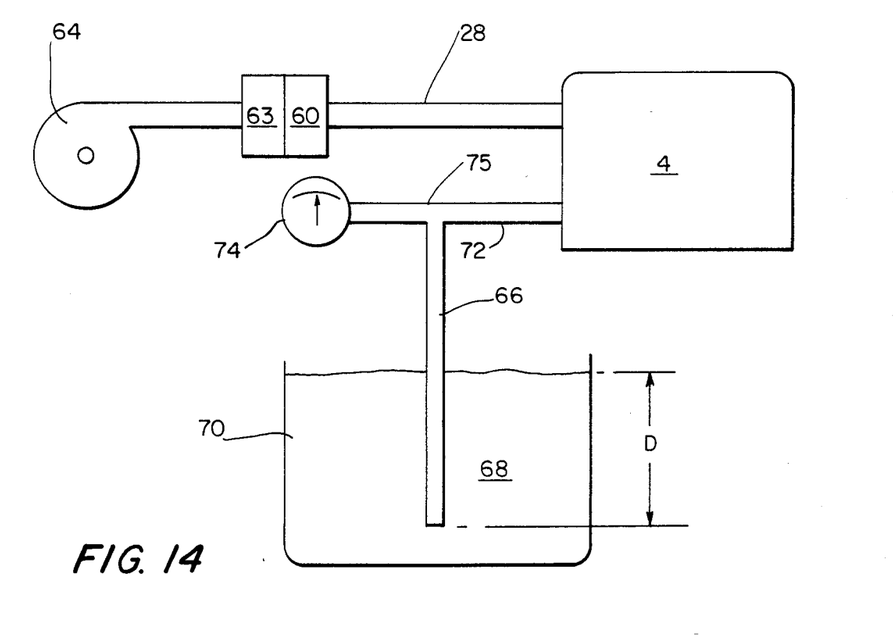
FIG. 14 is a schematic representation of a system useful for maintaining pressure within the work space and an eye when it is undergoing surgery.

A system for maintaining the pressure inside the chamber at levels up to 15 mm Hg. above atmospheric pressure, and higher, during open eye surgery is shown in FIG. 14. In it, a variable speed blower 64 blows air via humidifier 63, filter 60, and inlet hose 28 into upper enclosure 4. A low resistance air outflow pathway is provided via outflow hose 72 and pressure control tube 66. However, the end of control tube 66 is inserted to depth D in water 68 contained in receptacle 70. Thus, air cannot leave the chamber via this route until the pressure exceeds that corresponding to depth D when the air begins to bubble out the end of control tube 66. A depth D of about 20 cm. water corresponds to about 15 mm Hg. above atmospheric pressure. A depth D of about 13 cm. water corresponds to a pressure of about 10 mm Hg. above atmospheric pressure. A pressure gauge 74, measuring the actual pressure in the system, is connected to one arm of T-joint 75, the other two arms of the T-joint being used to connect outflow hose 72 to control tube 66. A desired pressure in the system can be established by adjusting the blower speed and the depth of the end of control tube 66 in water. By providing continuous bubbling of air out the end of control tube 66, the established pressure will be buffered to some extent against volumetric changes occurring within the chamber. For example, if the surgeon's forearm, which passes through a hermetic seal, is pushed further into the chamber, the volume in the chamber available for air will be reduced. Or, for example, if the forearm is withdrawn somewhat from the chamber so that the hermetic seal surrounds the forearm closer to the wrist, there will be more volume available for air in the chamber. Should the pressure rise or fall as a result of such volumetric changes, the air flow through control tube 66 will transiently either increase or decrease, respectively, tending to buffer the pressure.

Other systems may be employed for maintaining the desired pressure in the chamber. For example, a compressed air tank with a flow rate valve may be substituted for a blower. The features of each system can be designed to accommodate the particular requirements of the eye, the procedure, and the physician.

The purpose of including a humidifier in the source of air supply for enclosure 4 is to minimize drying of the patient's eye, particularly near the support ring where there may be leakage of air through interstices between the ring and the drapery and between the ring and the eye. The walls of the chamber can be kept warm to prevent condensation, by means of a heating element. Moisture can also be supplied by squirting balanced salt solution on areas tending to dry, as is done in conventional eye surgery.

Certain criteria should be observed when applying the teachings of the present invention. Thus, it is important that the structure of support 100, chuck carrier bar 101, ring 44, chuck 41, and the hold of chuck 41 on ring 44 be of sufficient rigidity so that the weight of the drape and the air pressure on the drape do not exert undue force upon the eye. The shaft of stem 43 may, for example, be made square to add rigidity to the hold on it by chuck 41. The drape itself must be of sufficient thickness to resist stretching by the air pressure applied to it. Also, it is important to assure that air pockets are not trapped under the drape, bounded by contact of the drape with the face and possibly in continuity with air space adjacent to movable structures which might press on the external surface of the eye outside the border of the designated surgical field. Further, the head must be properly immobilized to prevent displacement of the head and eye relative to the immobilized ring.

While the invention enables the surgeon to establish an elevated pressure within a working space adjacent to the surgical field during surgery, even before the incision is made, it will be apparent to those skilled in the art that the invention has particular utility in that it allows the surgeon broad latitude in the timing of the application of air pressure, as well as in the pressure level used. That is, the pressure level can be adjusted, maintained, or allowed to remain at atmospheric, as called for by particular surgical situations as they arise during an operation.

Variations from the "preferred embodiment" are possible both in the apparatus and in the sequence of attachment of the apparatus to the eye. These variations possess advantages and disadvantages. Some of the variations and some of the advantages and disadvantages will be discussed, further illustrating the concept.

The ring can be attached to the eye, stabilized to the base plate that lies beneath the patient's head, following which a drape having a preformed aperture can be placed over the face, the aperture then attached to the ring, and the upper enclosure then emplaced. This sequence would deny the surgeon further access to the ring support during surgery for fine adjustments because the ring support would lie beneath the drape.

In the alternative, the ring is attached to the eye first and the entire drape with preformed aperture is placed over the face, with the ring then brought up through the aperture. The upper enclosure with its immobilizing support is then positioned, and the immobilizing support is attached to the ring.

In another alternative, the drape with its preformed aperture is first placed on the eye. The upper enclosure is then placed, and the ring, while attached to its support apparatus on the wall of the upper enclosure, is brought down through the aperture onto the eye. The surgeon sews the ring to the eye, there being some interference by the aperture edges in close proximity to the ring, the surgeon displacing the aperture in different directions from time to time to provide sufficient exposure.

It will be apparent from the three variations above that the adhesive patch described with the preferred embodiment is not a necessity, though it could be used with some of the variations. One of its purposes, as described earlier, is to minimize the tendency of the drape and its aperture to shift from their proper positions in relation to the ring and eye when pressure is applied. This was achieved by determining the lie of the drape under pressure before the drape had an aperture, releasing the pressure, cutting an aperture, and laying in the adhesive patch with its sized aperture to close the cut hole and provide an aperture of the right size in the right position. Whether or not the adhesive patch is used, but especially if it is not used, the use of an adhesive undersurface on the drape by which the drape is caused to adhere to the patient's face would reduce the tendency of the drape to shift the aperture position when pressure is applied.

Finally, it will be understood that, in the interest of simplicity, customary details of the preparation of the patient and of the surgical equipment have been omitted from the preceding description of the invention and from the drawings. Thus, the sterile coverings customarily used around the neck and head of the patient have been omitted. Similarly, it will be apparent that the enclosure may be designed to position particular structural features conveniently for surgery on a left eye, and that a reversed form of enclosure may be organized to position the various structural features more conveniently for an operation on a right eye.

What I claim is:

1. A method for opposing deformity, displacement, and expulsion of ocular tissues during eye surgery of the types in which a cut is present through the ocular wall comprising the steps of:
   (a) generating an air pressure higher than ambient atmospheric pressure in a space outside the eye that bears upon a designated surgical field;
   (b) concurrent with step (a), maintaining those surfaces of the eye that lie outside the border of said designated surgical field at ambient atmospheric pressure;
   (c) concurrent with steps (a) and (b), stabilizing the eye against the applied pressure; and
   (d) concurrent with steps (a), (b), and (c), providing access of the surgeon to the designated surgical field.

2. The method of claim 1 wherein step (a) of generating an air pressure higher than ambient atmospheric pressure is comprised of the steps of:
   (e) assembling an air chamber having an aperture whose edges are coupled to the eye along the border of the designated surgical field; and
   (f) generating an air pressure higher than atmospheric in the chamber.

3. The method of claim 2 wherein the coupling of the chamber aperture to the eye is achieved by means of suturing.

4. The method of claim 2 wherein step (b) of maintaining those surfaces of the eye that lie outside the border of the designated surgical field at ambient atmospheric pressure is comprised of the steps of:
- (g) restraining any part of the chamber that might directly or indirectly bear upon those surfaces of the eye outside the border of said designated surgical field using chamber restraints; and
- (h) restraining the head of the patient from movement that might compress the eye against said chamber or said chamber restraints.

5. The method of claim 3 wherein step (c) of stabilizing the eye against the applied pressure consists of the step of:
- (j) stabilizing the eye along the border of said designated surgical field.

6. The method of claim 5 wherein step (d) of providing access of the surgeon to the designated surgical field is comprised of:
- (k) providing portals in the air chamber through which the hands of the surgeons or instruments may pass into the chamber and remain during surgery without causing substantial pressure change from the desired pressure level as a result of leakage between the portal and the object passing through it;
- (l) providing airlocks for the exchange of surgical instruments and materials into and out of the chamber if and when required by the surgical procedure to be done; and
- (m) providing transparency for enough of the chamber walls to permit observation of the surgery or building observation devices into the chamber walls.

7. The method of claim 6 wherein step (e) of assembling an air chamber includes the step of:
- (n) attaching a flexible drape to a chamber across an opening in said chamber so that the flexible drape becomes part of the wall of said chamber, and with the aperture in said chamber formed in the drape.

8. The method of claim 7 wherein the step of attaching a flexible drape to said chamber is comprised of the step of:
- (o) clamping the flexible drape using clamp means that compress the drape against a rigid portion of said chamber.

9. The method of claim 8 with the aperture of the chamber preformed in the flexible drape.

10. The method of claim 8 with the aperture preformed in a flexible adhesive patch, and further comprising the steps of:
- (p) cutting a hole in the flexible drape smaller than the size of the adhesive patch, but larger than the size of the patch aperture; and
- (q) applying the adhesive patch to the flexible drape over the hole in the drape so that the aperture of the patch, in effect, replaces the hole in the drape.

11. The method of claim 7 wherein step (g) is carried out by the flexible drape under pressure being restrained from bearing upon surfaces of the eye outside the border of the designated surgical field by the natural support effect of the bony structures of the patient's face.

12. The method of claim 7 wherein step (g) is carried out by the flexible drape under pressure being restrained from bearing upon the surfaces of the eye outside the border of the designated surgical field by the natural support effect of the bony structures of the patient's face and by appliances attached to the patient's face to alter the effective supportive contour of the patient's face.

13. The method of claim 12 further comprised of an adhesive undersurface on the drape and appliances to stabilize their position.

14. The method of claim 7 wherein step (g) is carried out by the flexible drape under pressure being restrained from bearing upon the surfaces of the eye outside the border of the designated surgical field by the natural support effect of the bony structure of the patient's face and the attachment of the drape to rigid parts of said chamber whose position is fixed relative to a rigid plate to which the patient's head is immobilized.

15. The method of claim 7 wherein step (g) is carried out by the step of:
- (r) adjusting the position and immobilizing the position of rigid protective structures between the surfaces of the eye outside the border of the designated surgical field and the flexible drape, to act as a shield for the eye against movement of the flexible drape under pressure.

16. The method of claim 7 wherein step (j), of stabilizing the eye along the border of the designated surgical field, is carried out by the flexible drape and its aperture whose edges are coupled to the eye along the border of the designated surgical field being supported by the natural support effect of the bony structures of the patient's face.

17. The method of claim 7 wherein step (j), of stabilizing the eye along the border of the designated surgical field, is carried out by the flexible drape and its aperture whose edges are coupled to the eye along the border of the designated surgical field being supported by the natural support effect of the bony structures of the patient's face and by appliances attached to the patient's face to alter the effective supportive contour of the patient's face.

18. The method of claim 17 further comprised of an adhesive undersurface on the drape and appliances to stabilize their position.

19. The method of claim 7 wherein step (j), of stabilizing the eye along the border of the designated surgical field, is carried out by the flexible drape and its aperture whose edges are coupled to the eye along the border of the designated surgical field being supported by the natural support effect of the bony structures of the patient's face and the attachment of the drape to rigid parts of said chamber whose position is fixed relative to a rigid plate to which the patient's head is immobilized.

20. The method of claim 7 wherein step (j) is carried out by the steps of:
- (s) coupling to the eye along the border of the designated surgical field a rigid closed loop contoured to lie against the eye along the border of the designated surgical field;
- (t) coupling the edges of the chamber aperture to the rigid closed loop; and
- (u) stabilizing the position of the rigid loop on the eye using a rigid but adjustable support structure connecting the rigid loop to a rigid part of said chamber that is in fixed relation to a rigid plate to which the head is immobilized.

21. The method of claim 20 wherein step (g) is achieved by the addition of rigid support projections attached to the rigid closed loop of step (s), these projections passing between the surface of the eye outside the border of the designated surgical field and the flexible drape, to act as a shield for the eye against movement of the flexible drape under pressure.

22. The method of claim 21 wherein the rigid loop is coupled to the eye by suturing.

23. The method of claim 22 wherein the coupling of the chamber aperture to the rigid loop is achieved by means of suturing.

24. The method of claim 22 wherein the coupling of the chamber aperture to the rigid loop is achieved by means of stretching an elastic aperture edge over the rigid loop so as to fit into a groove in the rigid loop.

25. The method of claim 22 wherein the coupling of the chamber aperture to the rigid loop is achieved by means of stretching an elastic aperture edge over the rigid loop so as to fit against a surface of the rigid loop.

26. The method of claim 22 wherein the coupling of the chamber aperture to the rigid loop is achieved by means of the weight of the drape under pressure causing the aperture edges to be in application to the surface of the immobilized loop.

27. The method of claim 7 wherein step (j) is carried out by the steps of:
   (s) coupling to the eye along the border of the designated surgical field a rigid closed loop contoured to lie against the eye along the border of the designated surgical field;
   (t) coupling the edges of the chamber aperture to the rigid closed loop; and
   (u) stabilizing the position of the rigid loop on the eye using a rigid but adjustable support structure connecting the rigid loop to a rigid plate to which the head is immobilized.

28. Apparatus for opposing deformity, displacement, and expulsion of ocular tissues during eye surgery of the types in which a cut is present through the ocular wall comprised of:
   (a) a chamber defining an enclosed air space having an aperture the size of a designated surgical field of the eye;
   (b) coupling means for attaching the aperture edges to the border of the designated surgical field of the eye;
   (c) pressurizing means for controlling the level of air pressure at or above atmospheric pressure in the enclosed space;
   (d) surgical access means for the surgeon, surgical assistants, and instruments to have access to the designated surgical field so that surgery can be performed while the enclosed space is pressurized at or above atmospheric pressure, and for the anesthesiologist to have access to the patient's airway which lies outside the pressurized space;
   (e) eye stabilizing means for supporting the eye against the air pressure on the designated surgical field;
   (f) eye shielding means for preventing said chamber from indenting that part of the external eye wall lying outside the border of the designated surgical field; and
   (g) head stabilizing means for preventing movement of the patient's head and eye against said chamber, said coupling means, said eye stabilizing means, and said eye shielding means.

29. The apparatus of claim 28 wherein the wall of component
   (a) is comprised in part of a flexible air resistant drape with said aperture present in the drape.

30. The apparatus of claim 29 wherein said chamber has rigid parts defining an opening and a gasket on said rigid parts and said drape is clamped across said opening in the enclosed air space to said gasket on said rigid parts.

31. The apparatus of claim 30 wherein said aperture is comprised of a flexible adhesive patch that is applied over a hole cut in the drape so that the aperture replaces the hole.

32. The apparatus of claim 31 wherein said aperture has an edge formed of elastic material.

33. The apparatus of claim 31 wherein said coupling means of component (b) comprise sutures.

34. The apparatus of claim 33 further comprised of an adhesive undersurface on the drape.

35. The apparatus of claim 31 wherein said coupling means of component (b) comprise:
   (h) a rigid closed loop contoured to be in contact with the eye wall along a continuous linear zone of contact that forms a closed loop along the border of the designated surgical field;
   (j) suture means for coupling the rigid loop to the eye; and
   (k) means for coupling the aperture edges to the rigid closed loop.

36. The apparatus of claim 35 wherein said means (k) for coupling the aperture edges to the rigid closed loop are sutures.

37. The apparatus of claim 35 wherein said eye stabilizing means of component (e) comprise:
   (l) said rigid closed loop;
   (m) said suture means for coupling said rigid loop to the eye; and
   (n) an adjustable rigid support structure fixing the position of the rigid closed loop in relation to a rigid plate to which the patient's head is stabilized.

38. The apparatus of claim 37 wherein said eye shielding means of component (f) include:
   (o) rigid projections extending from said rigid closed loop that pass between the undersurface of said flexible drape and those parts of the eyeball surface lying outside the border of the designated surgical field;
   (p) said rigid closed loop; and
   (q) said adjustable support structure.

39. The apparatus of claim 38 wherein said means (k) of coupling the aperture edges to the rigid closed loop are sutures.

40. The apparatus of claim 38 wherein said means of coupling the aperture edges to said rigid closed loop include a surface on the immobilized rigid closed loop to which the aperture edges are apposed by the weight of the drape under pressure.

41. The apparatus of claim 38 wherein said rigid closed loop has a groove and said means of coupling the aperture edges to said rigid closed loop comprise an elastic aperture stretched over the rigid closed loop so as to fit into said groove in the rigid closed loop.

42. The apparatus of claim 38 wherein said rigid closed loop has a surface and said means of coupling the aperture edges to said rigid closed loop comprise an elastic aperture stretched over the rigid closed loop so as to fit against said surface of the rigid closed loop.

43. The apparatus of claim 38 wherein said means of controlling the pressure at or above atmospheric of component (c) comprise a variable speed blower (64), a humidifier (63) and filter (60) connected to said blower, an inflow hose (28) connecting said filter and entering said chamber and an outflow hose (72) connecting the chamber to a T-joint (75) having one end connected to a pressure gauge (74) and another end immersed in water to a depth approximating the desired pressure in the chamber.

44. The apparatus of claim 38 wherein said means of controlling the pressure at or above atmospheric of component (c) comprise a source of compressed air, a humidifier (63) and filter (60) connected to said source of compressed air, an inflow hose (28) connecting said filter and entering said chamber and an outflow hose (72) connecting the chamber to a T-joint (75) having one end connected to a pressure gauge (74) and another end immersed in water to a depth approximating the desired pressure in the chamber.

45. The apparatus of claim 44 wherein said surgical access means of component (d) comprise portals in said chamber walls through which the surgeons may pass their arms and surgical instruments with hermetic seals around their arms or instruments, and further comprise transparent walls through which the surgeons can see the surgical field and walls incorporating the objective of a surgical microscope.

46. The apparatus of claim 45 wherein said hermetic seals consist of simple rubber diaphragms bonded across said portals in the chamber walls, the diaphragms having circular openings whose unstretched size is less than the size of the arms or instruments passing through them.

47. The apparatus of claim 46 wherein said surgical access means further comprise a passageway into the enclosed space having a first doorway opposite said enclosed space and a second doorway to the enclosed space which can be operated in sequence to permit passage of surgical instruments or material into and out of the enclosed space without substantial loss of pressure in the enclosed space.

48. The apparatus of claim 47 wherein said chamber and its supporting structures include an arch-like part which permits access to the nose and mouth of the patient.

49. The apparatus of claim 47 wherein said chamber includes a rigid upper enclosure, said eye shielding means of component (f) include a base frame (8) resting on a base plate (16), and anchored against lateral motion by pins protruding upwards from the base plate into holes in the base frame (14), the base frame (8) having an upwardly directed surface contoured to match that of a downwardly directed gasketed surface of said rigid upper enclosure (4) so that when a flexible drape (32) is laid over the base frame (8) and the upper enclosure (4) emplaced and clamped to the base plate (16), a pressure chamber is formed over the patient having rigid parts in fixed relation to the base plate (16) to which the patient's head is stabilized.

50. The apparatus of claim 49 wherein said head stabilizing means of component (g) comprises a rigid base plate having a stabilized head rest and straps and postmounted head holders to stabilize the head resting on its head rest to the base plate.

51. The apparatus of claim 29 wherein said chamber has rigid parts defining an opening and said drape is clamped across said opening in the enclosed air space to said rigid parts.

52. The apparatus of claim 51 wherein the drape has a reinforced edge or frame contoured to match the rigid parts of said chamber to which it is clamped.

53. The apparatus of claim 51 wherein said aperture is preformed in the drape.

54. The apparatus of claim 29 wherein said flexible air resistant drape is preformed to conform to facial contours around the eye.

* * * * *